(12) United States Patent
Fan et al.

(10) Patent No.: US 8,034,271 B2
(45) Date of Patent: Oct. 11, 2011

(54) PROCESS FOR MAKING COMPOSITE PRODUCTS FROM FIBROUS WASTE MATERIAL

(75) Inventors: Mizi Fan, Watford (GB); Peter William Bonfield, Codicote (GB)

(73) Assignee: Building Research Establishment Ltd., Watford, Hertfordshire (GB)

( * ) Notice: Subject to any disclaimer, the term of this patent is extended or adjusted under 35 U.S.C. 154(b) by 99 days.

(21) Appl. No.: 12/225,602

(22) PCT Filed: Mar. 23, 2007

(86) PCT No.: PCT/GB2007/050145
§ 371 (c)(1),
(2), (4) Date: Feb. 26, 2009

(87) PCT Pub. No.: WO2007/110661
PCT Pub. Date: Oct. 4, 2007

(65) Prior Publication Data
US 2009/0169812 A1    Jul. 2, 2009

(30) Foreign Application Priority Data

Mar. 25, 2006  (GB) .................................. 0606063.6

(51) Int. Cl.
*D21B 1/12* (2006.01)
(52) U.S. Cl. ......................... 264/115; 264/109; 264/914
(58) Field of Classification Search ........................ None
See application file for complete search history.

(56) References Cited

U.S. PATENT DOCUMENTS

| | | | |
|---|---|---|---|
| 2,030,626 A | 2/1936 | Ellis | |
| 3,741,863 A | 6/1973 | Brooks | |
| 4,072,273 A | 2/1978 | Reiniger | |
| 4,290,988 A | 9/1981 | Nopper et al. | |
| 4,407,771 A * | 10/1983 | Betzner et al. | 264/115 |
| 4,597,928 A | 7/1986 | Terentiev et al. | |
| 5,034,175 A * | 7/1991 | Safstrom | 264/120 |
| 5,624,616 A * | 4/1997 | Brooks | 264/83 |
| 6,017,475 A * | 1/2000 | Cantrell | 264/140 |
| 6,464,708 B1 | 10/2002 | Higuma | |
| 6,467,708 B1 | 10/2002 | Terzini et al. | |
| 6,596,209 B2 * | 7/2003 | Uhland et al. | 264/115 |
| 6,821,614 B1 | 11/2004 | Dubelsten et al. | |
| 2002/0084549 A1 | 7/2002 | Yang | |
| 2003/0160349 A1 * | 8/2003 | Wasylciw | 264/83 |

FOREIGN PATENT DOCUMENTS

| | | |
|---|---|---|
| DE | 39 02 023 | 7/1990 |
| DE | 39 02 023 A1 | 7/1990 |
| DE | 40 20 969 | 7/1991 |
| DE | 40 20 969 C1 | 7/1991 |
| DE | 40 37 836 A1 | 6/1992 |
| DE | 41 31 492 | 3/1993 |
| DE | 41 31 492 A1 | 3/1993 |
| DE | 197 56 129 A1 | 7/1999 |
| GB | 1 364 474 | 8/1974 |
| GB | 2 026 019 A | 1/1980 |
| GB | 2 317 623 A | 4/1998 |
| GB | 2 370 242 A | 6/2002 |
| GB | 2 392 161 A | 2/2004 |
| JP | 2003-12359 | 1/2003 |
| WO | WO 95/21129 | 8/1995 |
| WO | WO 98/25744 | 6/1998 |
| WO | WO 01/89730 A2 | 11/2001 |
| WO | WO 02/103113 A3 | 12/2002 |
| WO | WO 03/024633 A1 | 3/2003 |
| WO | WO2004/018767 * | 3/2004 |
| WO | WO 2004/041733 A1 | 5/2004 |

OTHER PUBLICATIONS

International Preliminary Report on Patentability mailed Oct. 9, 2008 for corresponding International application No. PCT/GB2007/050145.
International Search Report, dated May 30, 2007, corresponding to PCT/GB2007/050145.
British Search Report, dated Jun. 21, 2006, corresponding to GB0606063.6.

* cited by examiner

*Primary Examiner* — Mary Lynn F Theisen
(74) *Attorney, Agent, or Firm* — Christie, Parker & Hale, LLP

(57) ABSTRACT

A process for making composite products from waste material comprises the steps of a) obtaining fibrous material produced by the thermal treatment of waste materials with pressurized steam; b) mixing the fibrous material with a binding material; c) forming the resulting mixture into a shape; d) pressing the shaped mixture under pressure; and e) hardening the mixture; wherein the process also comprises the steps of the separating out the fibrous material and deodorizing the fibrous material. The waste material may be domestic bin liner waste.

30 Claims, 2 Drawing Sheets

PROCESS FOR MAKING COMPOSITE PRODUCTS FROM FIBROUS WASTE MATERIAL

CROSS-REFERENCE TO RELATED APPLICATION

This application is a National Phase Patent Application of International Application Number PCT/GB2007/050145, filed on Mar. 23, 2007, which claims priority of British Patent Application Number 0606063.6, filed on Mar. 25, 2006.

The present invention relates to a process for making composite products from fibrous waste material, and to the products made by this process. These products may be construction, insulation or packaging products. They may be used to make furniture or have applications in the transport (eg. automotive) or marine industries. The products may be board products.

Domestic waste comprises bulk household waste (for example carpets and furniture), seasonal household waste (for example grass cuttings) and household bin liner waste. It is estimated that the UK produces 30 million tonnes of household bin liner waste each year. This waste cannot be segregated without additional processing and is traditionally disposed of in landfill sites.

Various processes have been developed for processing household bin liner waste in order to reduce the amount of waste sent to landfill sites. For example, WO 2004/076083 discloses a method in which the waste is subjected to a high-pressure, high-temperature environment and is then subjected to bacterial digestion. The treated waste is used or disposed of in an environmentally acceptable manner, for example as compost.

WO 2004/018767 discloses a method of treating fibres produced by the thermal treatment of waste materials with pressurised steam. This thermal treatment occurs in an autoclave process. In such autoclave processes, domestic waste is fed into a rotating autoclave where it is sterilised using pressurised steam and broken down into organic and non-organic fractions. These fractions are screened to provide material for either recycling or disposal at landfill sites. Generally-speaking, such an autoclave process produces approximately 5% glass, 5% metal and 10% plastics material for recycling, approximately 70% biofibre material and approximately 10% inert material for disposal at landfill sites or for possible use as an aggregate. The biofibre material is currently incinerated or sent to landfill sites.

The method disclosed in WO 2004/018767 for treating fibres produced by the thermal treatment of waste material comprises drying the fibrous material to a moisture content in the range of from about 4 to about 15% by weight of the material; substantially removing debris from the fibrous material; and preferably reducing the length of the fibres in the fibrous material to less than 35 mm. The drying step and the removal of debris are both carried out in a drying apparatus. It is this treatment which is the main focus of this document.

Whilst this prior art document states that its treated fibres are suitable for use in the manufacture of gasified fuel, agglomerated solid fuel, wood replacement products, insulation materials and/or attenuation materials, there is no disclosure of how to turn the treated fibres into products other than fuels.

The fibres produced by an autoclave process, even when further treated in the manner disclosed in WO 2004/018767, are not readily usable and their dimensions and other properties vary considerably depending on the parameters of the autoclave process.

The present invention seeks to provide a process for making composite products, including construction, insulation or packaging products, from fibrous waste material. This reduces raw material costs since virgin raw materials can be replaced in whole or in part by recycled materials. Production costs are also reduced: the amount of material processing is reduced since the starting material is provided in a fibrous form. Further, the process has environmental benefits as household waste is recycled rather than sent to landfill sites. Also, the process provides low cost composite products for use in industries such as the construction, insulation, packaging, furniture, transport and marine industries.

Figure 1:
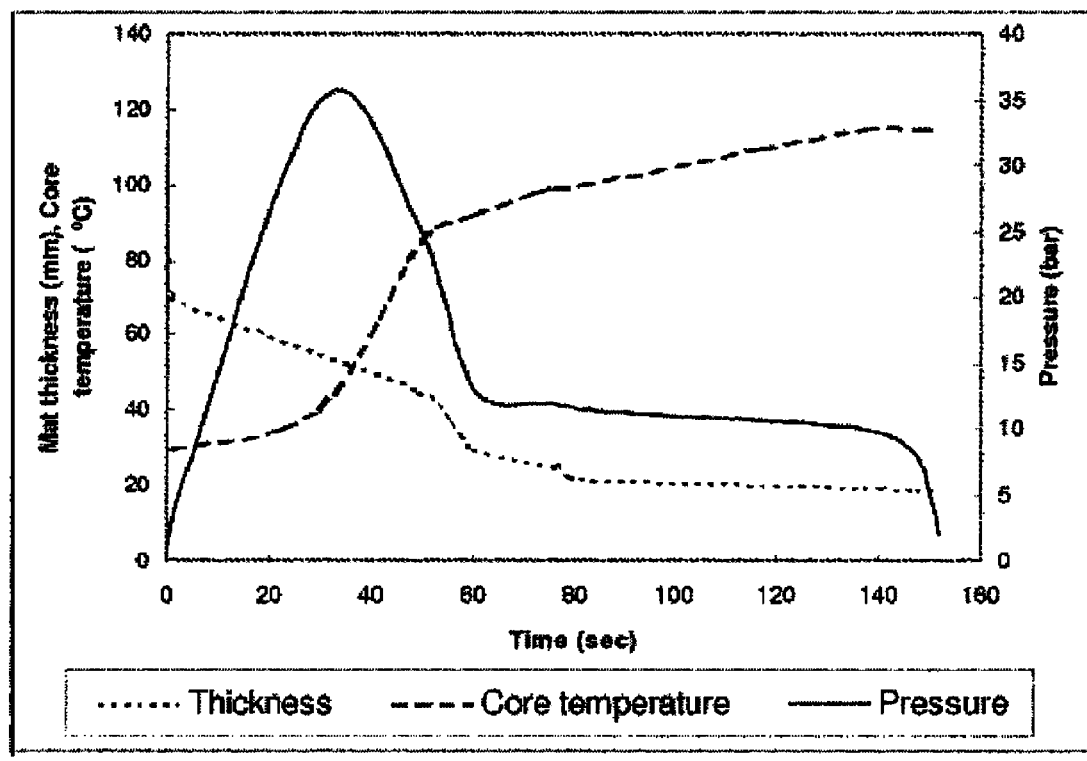
FIGS. 1 and 2 illustrate the hot pressing conditions according to the embodiments of the present invention.

A composite product is a complex material in which two or more distinct substances, such as glass and polymers, combine to produce structural or functional properties not present in any individual component.

According to the present invention, there is provided a process for making composite products from waste materials comprising:
a) obtaining fibrous material produced by the thermal treatment of waste materials with pressurised steam;
b) mixing the fibrous material with a binding material;
c) forming the resulting mixture into a shape; and
d) curing the shaped mixture;
wherein the process also comprises the steps of the separating out the fibrous material and deodorising the fibrous material.

According to the present invention, there is also provided a process for making construction, insulation or packaging products comprising:
a) obtaining fibrous material produced by the thermal treatment of waste materials with pressurised steam;
b) mixing the fibrous material with a binding material;
c) forming the resulting mixture into a shape; and
d) curing the shaped mixture;
wherein the process also comprises the steps of the separating out the fibrous material and deodorising the fibrous material.

Preferably the waste material is domestic waste material, more preferably it is domestic bin liner waste material. Domestic bin liner waste material generally comprises about 60 to 70 wt % cellulosic materials, about 10 wt % mixed plastics and about 10 wt % metal. Domestic bin liner waste material generally comprises paper, textiles, cardboard, plastic, food, metal and glass.

The fibrous material is obtained using an autoclave process. It is of low quality and is therefore not useful in papermaking or other processes that require the use of high quality, clean fibres.

The separating out step may be carried out using a raking and shearing process; by puffing and/or refining; or by mixing the fibrous material with a powdered material, such as cement.

The deodorising step may be carried out by adjusting the moisture and/or temperature of the inner layer of the fibrous material with respect to the outer layer of the fibrous material. Alternatively, the deodorising step may be carried out by treating the fibrous material with a lime solution; by adding calcium carbonate to the fibrous material; or by adding cement to the fibrous material in an aqueous environment. In another embodiment, the deodorising step is carried out by enveloping the fibrous material in a polymeric material, an example being plastic.

Preferably, the fibrous material obtained in step a) has a moisture content in the range of from 4 to 10% by mass; a cold water soluble content in the range of from 10 to 20% by mass; a hot water soluble content in the range of from 9 to 17% by mass, more preferably from 10 to 16% by mass; and an alkali soluble content in the range of from 12 to 25% by mass, more preferably from 14 to 24% by mass.

It is preferred that the fibrous material obtained in step a) comprises fibres being less than 10 mm in length and/or having a mean length of less than 5 mm. Preferably the fibres in the fibrous material are less than 8 mm in length, more preferably less than 7 mm in length and most preferably less than 6 mm in length. Preferably the fibres in the fibrous material have a mean length of less than 4 mm, preferably less than 3 mm.

The binding material may be selected from the group consisting of adhesive, cement and polymeric material. The polymeric material may be mixed with wax prior to use. When resin is used as a binding material, the amount of resin used in the process may be from 2 to 20% by mass, preferably 9 to 12% by mass, of oven-dry fibrous material.

Preferably, the fibrous material is dried to a moisture content of less than 8% by mass, preferably in the range of from 4 to 8% by mass, and more preferably about 6% by mass, prior to its mixing with the binding material.

The forming step may comprise pressing and/or extruding. The pressing step may be carried out at an elevated temperature. The pressing step may be carried out for a duration of 10 to 30 seconds per millimeter, preferably 16 to 20 seconds per millimeter. The pressing step may be carried out at a pressure of 1 MPa to 4 MPa. Extrusion is particularly suitable for forming plastic fibre board products.

The process preferably comprises a final drying step.

Board products such as particle fibre board, medium density fibre board, cement bonded fibre board, gypsum fibre board, soft board (useful for insulation and packaging) and plastic fibre board may be prepared by the process of the present invention. These products may be provided with one or more surface treatments selected from the group consisting of veneering, painting and polishing. These surface treatments may be on one or both of the major surfaces of a board product.

The products made using fibrous waste material in accordance with the present invention may be manufactured using phase-change materials, such as BASF AG's Micronal® PCM, in the manufacturing process.

These products may be construction, insulation or packaging products. They may be used to make furniture or have applications in the transport (eg. automotive) or marine industries.

In one example, the present invention provides a pressed board product comprising autoclaved fibres recovered from domestic bin liner waste, the product comprising from 9 to 12 wr % resin and wax, the board being a uniform composite material.

The present invention also relates to the use of fibrous material produced by the thermal treatment of waste materials with pressurised steam in the manufacture of composite products, including construction, insulation or packaging products.

Embodiments of the present invention will now be described, by way of example only.

Fibres

Six bundles of fibrous material (labelled types 1 to 6) obtained by autoclave processes were analysed to ascertain their properties and thus their suitability for making board products.

Type 1 and type 2 materials: Both types of fibrous materials contained long and thin fibres in fibre bundles. The ratio of the fibre length to diameter was higher than the rest of the fibrous materials (types 3 to 6). The type 1 material had a more consistent size of fibre in the fibre bundles than the type 2 material, and, therefore, the type 1 material was preferred.

Type 3 material: the general conversion process of domestic waste results in a high percentage of type 3 fibrous materials. This material contains short and fine fibrous materials.

Type 4 and type 5 materials: These materials were in the form of fibre bundles and particles. They were derived before a final separation into the type 1 or type 3 fibrous materials. As with type 1 and type 2 fibrous materials, the type 4 material is more consistent in size compared to the type 5 material, so the type 4 material was preferred.

Type 6 material: This material was obtained before any drying process. This means that for some types of construction products (e.g. cement bonded products), it may not be necessary to dry the raw material to a low moisture content.

1. Moisture Content

The moisture content (MC) of the raw material samples was determined by oven-drying. A portion of each material sample was weighed into a tare weighing bottle and placed in a laboratory oven at 104° C. overnight. After cooling, the samples were re-weighed and their moisture contents were calculated.

The moisture content of the selected materials is given in Table 1. It can be seen that the mean moisture content of the type 1 material was much higher than that of both the type 3 and type 4 materials. This indicates the effect that the composition of the domestic waste has on the properties of the treated fibrous materials and consequently the performance of the construction, insulation and packaging products made therefrom.

It is noted that air generally has a moisture content of 8 to 10% by mass, so that when fibrous material has a moisture content in this range it is generally considered to be in equilibrium with its environment.

TABLE 1

Mean moisture content of three selected fibrous materials

| Material | Mean MC (%) by mass |
|---|---|
| Type 1 | 8.71 |
| Type 3 | 6.52 |
| Type 4 | 5.95 |

2. Water Solubility

Cold Water Solubility

Approximately 2 g of each sample was taken and weighed into a 400 ml beaker. 300 ml of water was added and allowed to soak for 48 hours, followed by periodic stirring (for a total of approximately 16 hours). After this time, the mixtures of raw material and water were filtered into tare crucible filters, oven-dried at 104° C. overnight and re-weighed. The cold water soluble content of each sample was calculated from the difference between the original weight (corrected for moisture content) and the final dry weight.

Hot Water Solubility

Approximately 2 g of each sample was taken and weighed into 350 ml conical flasks and 100 ml of water was added. The water was brought to the boil and simmered for 3 hours. After this time the mixtures of raw material and water were filtered into tare crucible filters, washed with hot water and oven-dried at 104° C. overnight and re-weighed. The hot water soluble content of each sample was calculated from the difference between the original weight (corrected for moisture content) and the final dry weight.

The results are given in Table 2 and Table 3. The soluble contents of the type 3 material were lower than that of the type 1 and type 4 materials. This again indicates the effect of the waste composition on the properties of the derived fibrous materials. The cold and hot water soluble contents will affect both the process of making construction, insulation and packaging products and the performance of the products made.

TABLE 2

Cold water soluble content

| Material | Cold water soluble content (%) by mass |
|---|---|
| Type 1 | 16.71 |
| Type 3 | 11.15 |
| Type 4 | 19.25 |

TABLE 3

Hot water soluble content

| Material | Hot water soluble content (%) by mass |
|---|---|
| Type 1 | 12.54 |
| Type 3 | 10.61 |
| Type 4 | 15.90 |

3. Alkali Solubility

Approximately 2 g of each sample was taken and weighed into 400 ml beakers and 100 ml of 1% sodium hydroxide solution was added and simmered for 1 hour. After this time the mixtures of raw material and alkali solution were filtered into tare crucible filters, washed with hot water and oven-dried at 104° C. overnight and re-weighed. The alkali soluble content of each sample was calculated from the difference between the original weight (corrected for moisture content) and the final dry weight.

The results are given in Table 4. Again, it can be seen that the alkali soluble content of the type 3 material was only about 62% that of the type 1 material which had an alkali soluble content that was similar to that of the type 4 material. The alkali soluble content is an important consideration for the processing of the products, due to the alkali or acid sensitivity of the organic or inorganic binding material used.

TABLE 4

Sodium hydroxide (1%) soluble content

| Material | Alkali soluble content (%) by mass |
|---|---|
| Type 1 | 23.73 |
| Type 3 | 14.73 |
| Type 4 | 21.13 |

4. Fibre Length

The length of fibres in the raw material samples was measured by dispersing a small quantity of the raw material in water and dropping the dispersion onto a microscope slide. After evaporation of the water, the slide was placed in a magnifying projector microscope, the magnified images of the fibres were measured with a ruler and compared with a magnified calibrated scale.

The mean fibre length for the three selected fibrous materials is given in Table 5 and the percentage of various lengths of fibres in the fibre bundles is given in Table 6. As expected, the length of the type 1 material was higher than that of both the type 3 and type 4 materials (Table 5). The type 3 material had the highest percentage of short fibres (Table 6) compared with the type I and type 4 materials.

TABLE 5

Fibre length

| Material | Min length (mm) | Max length (mm) | Mean length (mm) |
|---|---|---|---|
| Type 1 | 0.9 | 5.6 | 2.2 |
| Type 3 | 0.3 | 5.6 | 1.1 |
| Type 4 | 0.5 | 3.3 | 1.3 |

TABLE 6

Content of various sizes of fibres

| Material | 0-1 mm | 1-2 mm | 2-3 mm | 3-4 mm | 4-5 mm | 5-6 mm |
|---|---|---|---|---|---|---|
| Type 1 | 10.70% | 39.30% | 17.90% | 35.70% | 0% | 3.60% |
| Type 3 | 55.60% | 37.00% | 3.70% | 0% | 0% | 3.70% |
| Type 4 | 47.60% | 33.33% | 12.70% | 4.80% | 0% | 0% |

Processing the Fibrous Material

One or more of the different types of fibrous material produced by the autoclave process were selected and analysed for their suitability for the product to be manufactured.

In the manufacture of products such as construction, insulation and packaging products from waste fibrous material, the solubility parameters of the fibrous material is useful to know as they can determine how much and what resin to add in order to achieve the desired end product. For example, if the fibre lengths are short then more resin can be added, and vice versa. The strength of the product is effectively built in after a chemical analysis of the autoclave product and by using fibre length and resin quantities.

During the manufacture of the product, the following two steps take place.

1) Separating Out the Fibrous Material

The fibrous material is separated out. This has as one of its objects the separation of tangles and bundles of the fibrous material, since the material forms bundles or blocks during the autoclave process. One way of achieving this separating out is by a rake-shear process. The present inventors have developed this to stretch the fibres and to break down fibre bundles. Traditional refining methods (e.g. hammer-mill processes) are not suitable as they mechanically damage the fibres.

The rake-shear process uses a pair of rake plates which are spaced apart and are driven in opposite directions by a motor. The distance between the plates and the length of the raking teeth depends on the fibrous material to be processed. By way of example, the length of the plate teeth is 2 to 5 mm for type 1 and type 2 materials and is 1 to 3 mm for type 3 and type 4 materials.

Another way of separating out the fibrous material is by puffing. In this process, air, usually at room temperature, is blown on the fibrous material. This increases its volume so that it appears puffed. This process is particularly useful for the manufacture of medium density fibre boards and softboards (ie insulation and packaging boards).

An additional method of separating out is to mix the fibrous material with cement during a first mixing stage in the manufacture of cement bonded products.

2) Deodorising the Fibrous Material

This process step removes or eliminates the odour of the fibrous materials. One such method is known as a 'media-gradient' process which is often used in the treatment of new timber. The present inventors have found that it is useful in deodorising the fibrous materials produced by the autoclave process. This method accentuates the difference of moisture or temperature between inner and outer layers of the fibrous material by adjusting the moisture and/or temperature of these layers. This may be achieved by the process step which dries the fibrous material to a desired moisture content. During this drying process, several cycles of heating the fibrous material may be carried out.

Another suitable method is a lime media treatment. By way of example, 10% lime solution is used. Alternatively, other chemicals may be used, such as adding calcium carbonate to the fibrous material in order to deodorise it. In this case, the humidity and temperature of the mixture is preferably controlled in order to provide an alkaline environment. In the manufacture of cement bonded products, the alkaline environment produced by the cement during the manufacturing process has the effect of deodorising the fibrous material. In the manufacture of plastic fibre boards, substantially enveloping the fibrous material in polymeric material deodorises the fibrous material.

The specific parameters used to deodorise are dependent on the shapes of the fibres in the fibrous material and on the dimensions of the end product. Two useful procedures are:

(1) A drying/heating-wetting process: the fibrous material is exposed to 80% relative humidity for 24 hours and then heated at 180° C. for three hours. This cycle can be repeated, depending on the condition of the fibrous material.

(2) Alkali treatment: the fibrous material is soaked for 24 hours in a 10% solution of $CaCO_3$ or similar.

A. Manufacture of Particle Fibre Board Products

The type 3 and 4 materials were selected as having properties suitable for use in the manufacture of particle fibre board products.

The fibre boards were manufactured from these fibrous materials using the following process steps, which have been found by the inventors to be generally applicable to the formation of particle fibre board products using the waste fibrous material obtained from an autoclave process:

a) Drying

The moisture content of the fibrous materials depends on their storage conditions. The materials are dried using the processes traditionally used in particle board manufacture (for example, using a drum dryer) to less than 8% by mass moisture content, preferably between 4 and 8% by mass moisture content, and most preferably about 6% by mass moisture content. This drying step has the effect of deodorising the fibrous material.

The final moisture content of the fibrous materials affects the amount and type of the resin to be used. Also, fibrous materials that are too wet require longer pressing times, reduce the production capacity and cause steam blisters in the fibre board core during hot pressing, which consequently results in low strength of the fibre boards. Fibrous materials that are too dry create a risk of fire, result in the fibres being too fine, increase the costs and energy consumption, and affect the wetability of the selected resin and the quality of the final products.

A suitable resin to use is MDI (methylene-diphenol-diisocyanate) because it is compatible with fibrous materials having a moisture content of about 6% by mass.

b) Mixing with a Binding Material

The fibrous materials are blended with resin and other additives. This has the effect of separating out the fibrous material. The amount and type of resin added is determined by the solubility parameters of the starting material in order to achieve the desired end product.

The resin must be mixed completely and homogeneously with wax within a short time prior to spreading it onto the fibrous materials. The dosed resin is distributed by means of centrifugal jets to the fibrous materials which are kept in a tumbling movement.

The parameters of the process in this experiment were as follows:

Type of resin: MDI.

Content: 10-12% by mass of the oven dry fibrous materials,

Wax: 1.5-2.0% by mass of the oven dry fibrous materials,

Duration: 2.5-3.0 minutes.

c) Forming the Mixture into a Shape

The fibrous materials are spread by blowing them onto a surface bordered by a frame of the size of the fibre board to be produced. The purpose of this process is to prepare a consistently uniform mat of resinated fibrous materials, before subjecting it to subsequent fabricating operations which, by pressure, or by pressure and heat, reduce the mat thickness to that of the desired fibre board, and simultaneously cure the binding agent to convert the product into a solid fibre board. The thickness of the mat is 10 to 20 times as thick as the final thickness of the product.

d) Cold Pre-Pressing

This is designed to reduce the thickness of the mat, to increase the contact of fibrous materials and to build an initial strength of the mat to facilitate further processing (eg. conveying and hot pressing). The thickness of the mat is about a quarter to a third that of the original thickness of the mat.

Other parameters of the process used in this experiment are:

Temperature: room temperature

Pressure: 13-18 bar

Time: 10-30 sec.

Spring back: 12-25%.

e) Hot Pressing

The schedule for hot pressing is illustrated in FIG. 1.

A low temperature process should be chosen, that is 170-180° C.

The press/heating factor in this experiment was about 8 sec/mm.

A longer pressure release time is required to ensure a gentle release of gas pressure inside the fibre board. This hot pressing cures the fibre board.

f) Finishing

Finishing includes cutting, thickness monitoring, weighing.

The particle fibre boards formed using this process are light grey to black in appearance. Thus, for some end uses they are veneered with products such as melamine or natural wood, or painted.

The table below sets out the properties of the fibre boards manufactured using the above process. It can be seen that the fibre boards so made meet the requirements for the relevant standard products.

TABLE 7

Properties of particle fibre boards (12 mm)*

| Type | Density (kg/m³) | TS (%) | IB (N/mm²) | MOE (kN/mm²) | MOR (N/mm²) |
|---|---|---|---|---|---|
| T3 raw fibre | 700-820 | 12.6 | 0.52 | 2260 | 16.22 |
| T4 raw fibre | 680-750 | 13.1 | 0.43 | 2550 | 17.10 |
| P2 | — | — | 0.28 | — | 12.5 |
| P3 | — | — | 0.40 | 1800 | 14.0 |
| P4 | — | 16 | 0.40 | 2300 | 17.0 |
| P5 | — | 11 | 0.45 | 2550 | 18 |

*TS = thickness swelling; IB = internal bond; MOE = modulus of elasticity; MOR = modulus of rupture.
P2 = Requirements for general purpose fibre boards for use in dry conditions
P3 = Requirements for fibre boards for interior fitments (including furniture) for use in dry conditions
P4 = Requirements for load bearing fibre boards for use in dry conditions
P5 = Requirements for load bearing fibre boards for use in humid conditions
P1 to P5 refer to the parts (ie Part 1 to Part 5) of the Standard BSEN312, this being a British Standard (BS) which is a European Harmonised Standard (EN), relating to the specifications of Particleboard.

Thickness swelling, when mentioned in this specification, is measured according to BSEN317 Particleboard and fibreboards: Determination of thickness swelling after immersion in water.

The Internal Bond, when mentioned in this specification, is measured according to BSEN319 Particleboards and fibreboards: Determination of tensile strength perpendicular to the plane of the board.

The Modulus of Elasticity and the Modulus of Rupture, when mentioned in this specification, are measured in accordance with BSEN310 Wood based panels: Determination of modulus of elasticity in bending and of bending strength.

B. Manufacture of Medium Density Fibre Board Products

The type 1 and 3 materials were selected as having properties suitable for use in the manufacture of medium density fibre board products.

The fibre boards were manufactured from these fibrous materials using the following process steps, after the fibrous material had been deodorised using 10% lime solution. The inventors have found these process steps to be generally applicable to the formation of medium density fibre board products using the waste fibrous material obtained from an autoclave process.

a) Refining

This step separates out the fibrous material. A grinding machine may be used. In this experiment, this step was carried out under a pressure of 7 to 8.5 bar for 3 to 5 minutes.

b) Drying

This is performed using a blow-line process which is connected to a continuous, long flash drier. The materials are dried to less than 8% by mass moisture content, preferably between 4 and 8% by mass moisture content, and most preferably about 6% by mass moisture content.

c) Mixing with a Binding Material

The fibrous materials are blended with resin and other additives. The amount and type of resin added is determined by the solubility parameters of the starting material in order to achieve the desired end product.

The resin must be mixed completely and homogeneously with wax within a short time prior to spreading it onto the fibrous materials. The dosed resin is distributed by means of centrifugal jets to the fibrous materials which are kept in a tumbling movement. The parameters of the process used in this experiment were as follows:
Resin: MDI
Content: 10-12% by mass oven dry fibrous materials.
Additives: Paraffin wax (emulsified)
Wax content: 1.5-2.0% by mass oven dry fibrous materials
Moisture content after mixing and drying: 10-12%
Fibrous material temperature: 30° C. before hot pressing.

d) Puffing

This step further separates out the fibrous material.

e) Forming

An air separation system (cyclone system) releases the dried fibres into a forming bin and mattresses are formed by the addition of a known mass of fibres into a continuous press steel belt/forming box. Water may be sprayed onto the surface during this step.

f) Cold Pre-Pressing

This is designed to reduce the thickness of the mat, to increase the contact of fibrous materials and to build an initial strength of the mat to facilitate further processing (eg. conveying and hot pressing). The thickness of the mat is about a quarter to a third that of the original thickness of the mat. Other parameters of the process used in this experiment were:
Temperature: room temperature
Pressure: 13-18 bar
Time: 10-30 sec.
Spring back: 12-25%.

g) Hot Pressing

Figure 2:
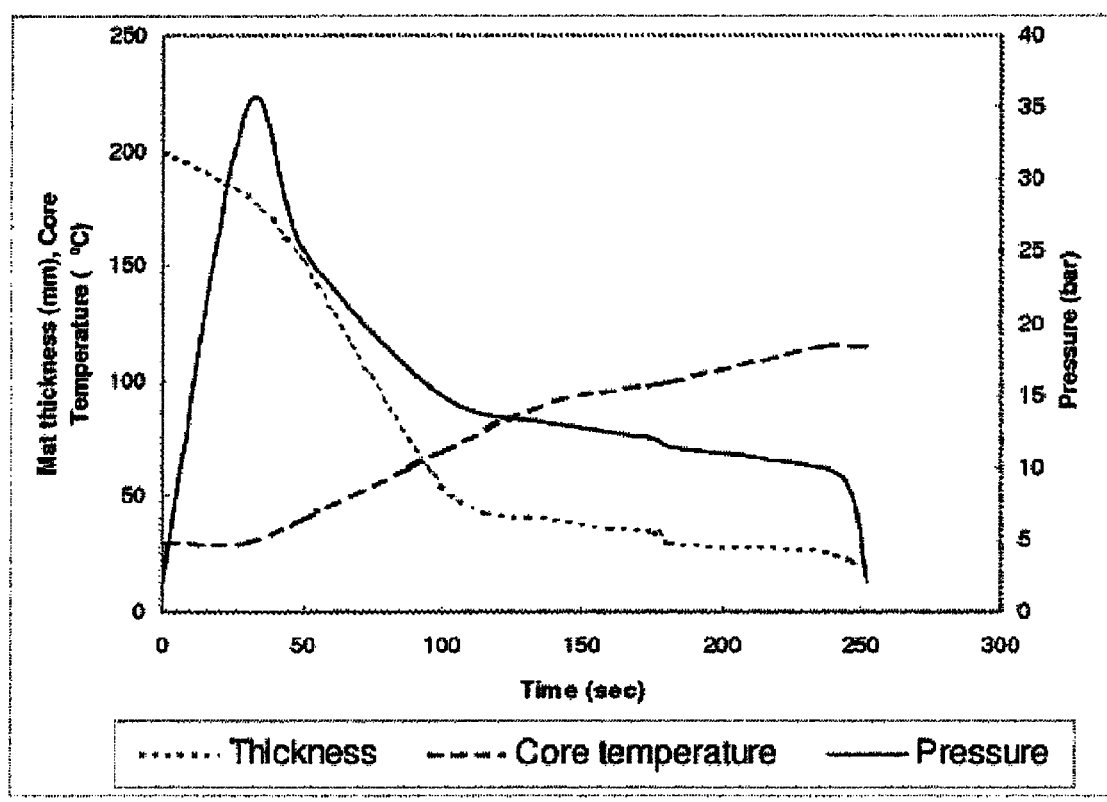

The conditions for hot pressing are set out in FIG. 2.

A low temperature process should be chosen, that is 165-175° C.

The press/heating factor used was about 15 sec/mm.

A longer pressure release time is required to ensure a gentle release of gas pressure inside the fibre board. This hot pressing cures the fibre board.

h) Finishing

Finishing includes cutting, thickness monitoring, weighing.

i) Optional Post Treatment

Heat treatment and humidification can be used to improve the quality of the products.

The particle fibre boards formed using this process are light grey to black in appearance. Thus, for some end uses they undergo a surface treatment such as being painted or being veneered with products such as melamine or natural wood.

The table below sets out the properties of the fibre boards manufactured using the above process. It can be seen that the type 1 material makes superior products to that of the type 3 material. It can also be seen that the properties of the end product vary, such that it is possible to adapt the process to derive a product with desired properties.

TABLE 8

Summarised properties of Medium Density Fibre board made from type 1 and type 3 Fibrous Material*

| Fibrous material | Density (kg/m³) | TS (%) | IB (N/mm²) | MOE (kN/mm²) | MOR (N/mm²) |
|---|---|---|---|---|---|
| Type 1 | 650-750 | 13 | 0.48 | 2630 | 18.22 |
| Type 3 | 900-1000 | 15 | 0.55 | 2250 | 15.12 |

*TS = thickness swelling; IB = internal bond; MOE = modulus of elasticity; MOR = modulus of rupture The following table compares the properties of medium density fibre board made from the type 1 fibrous material with conventional medium density fibre board. It can be seen that the fibre board made in accordance with the present invention has properties similar to that of conventional MDF and meets the requirements set for conventional medium density fibre board products.

TABLE 9

Summarised properties of Medium Density Fibre board (12 mm)*

| Fibrous material | Density (kg/m³) | TS (%) | IB (N/mm²) | MOE (kN/mm²) | MOR (N/mm²) |
|---|---|---|---|---|---|
| MDB (type 1) | 650-750 | 11.5 | 0.66 | 2630 | 24.88 |
| Conventional MDF | MDF | 12 | 0.55 | 2200 | 20 |
|  | MDF.H | 8 | 0.75 | 2400 | 24 |
|  | MDF.LA | 12 | 0.6 | 2500 | 25 |
|  | MDF.HLS | 8 | 0.75 | 2700 | 30 |

*TS = thickness swelling; IB = internal bond; MOE = modulus of elasticity; MOR = modulus of rupture
MDB = Medium Density Fibre Board made from the type 1 waste material
MDF = Requirements for general purpose fibre boards for use in dry conditions
MDF.H = Requirements for general purpose fibre boards for use in humid conditions
MDF.LA = Requirements for load bearing fibre boards for use in dry conditions
MDF.HLS = Requirements for load bearing fibre boards for use in humid conditions These requirements are from the British Standard BSEN622-5 relating to the specification of fibreboards; they are taken from Part 5 of this British Standard which relates to the requirement for dry process board (MDF).

The medium density fibre board process is suitable for use during a process for making insulation or packaging products from the waste fibrous material.

C. Manufacture of Cement Bonded Fibre Board Products

In cement composites, the cement needs to be hydrated extensively or completely in order to provide satisfactory physical and mechanical properties. The addition of waste fibrous material to cement, where the cement is able to hydrate correctly, was found to have the effect of minimising cracking and reducing the density of the product. The hydration process of a waste fibre/cement mixture was found to consist of four stages, namely stage 1—rapid initial hydration, stage 2—dormant period, stage 3—setting phase, stage 4—hardening phase.

During the dormant period (stage 2), dicalcium and tricalcium silicates are hydrated to form tobermorite gel and calcium hydroxide. The calcium hydroxide increases the pH of the cement paste to approximately 12.5, producing a highly alkaline paste which can swell, dissolve and degrade fibre. This has the effect of deodorising the fibrous material.

The type 1, 3 and 4 materials were selected as having properties suitable for use in the manufacture of cement bonded fibre board products. The type 6 material could also be advantageously used as it would not require drying prior to incorporating it in a mixture of cement, water and other components.

The fibre boards were manufactured from these fibrous materials using the following process steps. The inventors have found these process steps to be generally applicable to the formation of cement bonded fibre board products using the waste fibrous material obtained from an autoclave process.

a) Optional Refining

This optional step separates out the fibrous material, depending on the type of material being processed. This may be carried out under a pressure of 7 to 8.5 bar for 3 to 5 minutes.

Whether or not a refining process is included in the process, the type 1, 3 or 4 materials can be used for cement bonded fibre board.

b) Mixing

Prior to mixing the components of the product in the order listed below, an optional first step is to mix the fibrous material with some cement to separate out the fibres, if they have not been previously separated out using another method.

To make the cement bonded fibre board, the fibrous materials and cement are mixed with about 3% aluminium sulphate, 3% sodium silicate and water. Individual components are metered in relation to the weight the fibrous materials would be when absolutely dry. In practice, the moisture in the fibrous material is continuously monitored and taken into account with respect to the amount of water added. A basic mixture is about 65% cement and 35% fibrous material by weight, depending on the properties required of the end product.

The order of adding the components to the fibrous material is:

1) water
2) aluminium sulphate
3) sodium silicate
4) cement

For fibrous materials with a known moisture content, the water required for the manufacture of a cement bonded fibre board can be calculated from the equation:

$$W = 0.35A + (0.3 - MC)B \qquad (1)$$

Where:
W is the water requirement
A is the weight of cement
MC is the (oven dry) moisture content of fibrous materials
B is the weight of absolutely dry fibrous materials.

In this experiment, ordinary Portland cement was used.

The fibrous material is distributed randomly within the fibre board, whilst trying to avoid the formation of fibrous agglomerates during the wetting of the dry cement/fibre mixture. The moisture content of the waste fibres is increased before adding the cement.

The water to cement ratio has been found to have a significant effect on the hydration process of waste fibre/cement mixtures. In one example, using the type 3 fibrous material, the water to cement ratio required for optimum hydration was 0.39 for 5% by mass fibrous material, 0.37 for 10% by mass fibrous material, 0.43 for 20% by mass fibrous material and 0.48 for 30% by mass fibrous material. Of these, the composites made using a water to cement ratio in the range 0.3 to 0.4 performed best. Thus, composites having less than 20% by mass fibrous material were preferred, with less than 10% by mass fibrous material being more preferred.

The addition of cement to the fibrous material has the effect of deodorising this waste material in view of the alkaline environment produced as a result.

c) Forming

The accuracy of the thickness of finished fibre boards is dependent on the quality of forming, and this makes it important to keep the spreading accurate and constant within narrow limits. The thickness of formed fibre boards is three to three and a half times that of the final product. In the present example, the cement bonded fibre boards had the dimensions 700×700×15 mm.

d) Optional Cold Pre-Pressing

A pre-press process can be carried out for ease of mat handling and pressing.

e) Hot Pressing

The fibre board 'blanks' are arranged by a means of a stacker into stacks in holding frames. The stacks are compacted to a predetermined thickness in a press and fixed by a cover in the holding frame. The parameters for the press in this experiment were as follows:

Pressure: 25-30 bar
Time: 15 minutes f) Hardening

The stacks of fibre boards fixed in the mounting carriage are pre-hardened in a hardening tunnel with heating. The parameters for this experiment were as follows:
Temperature: 75° C.
Time: 7 to 8 hours
The fibre boards are subsequently de-stacked and trimmed.

g) Curing

The fibre boards are kept in a curing store. The conditions used were as follows:
Temperature: room temperature
Time: 7 to 8 days in which hydration takes place.

h) Drying (Conditioning)

In order to achieve the required properties and moisture content, the fibre boards are transferred to an oven. The conditioning parameters used in this experiment were:
Temperature: 100-115° C.
Time: 3-5 hours depending on the thickness
Final moisture content: 8-9% by mass.

i) Finishing

Depending on the application of the end product, the fibre boards can be polished on one or both sides.

The table below sets out the properties of the fibre boards manufactured using the above process.

The results show that all three types (1, 3 and 4) of the fibrous materials can be used to produce cement bonded fibre board, although superior cement bonded fibre board was made by using the type 1 and type 4 fibrous materials than by using the type 3 fibrous materials. The fibre size is more important than the soluble contents of the fibrous materials for dictating the performance of the products developed.

General cement bonded particle fibre board contains 30% wood chips by mass. The present inventors have therefore discovered that it is possible to replace wood chips with waste fibrous materials in the manufacture of cement bonded products.

The performance of cement bonded fibre boards was evaluated in accordance with British Standards BSEN634-1 relating to the specification of cement bonded particleboards—Part 1: general requirements and BSEN634-2 relating to the specification of cement bonded particleboards—Part 2: requirements for OPC bonded particleboards for use in dry, humid and exterior conditions. It can be seen that the cement bonded fibre boards made meet the requirements of the relevant British Standards for cement bonded particle board (see Table 10). The properties are dependent, amongst other things, on the percentage of fibrous materials included.

TABLE 10

Properties of Cement Bonded Fibre board*

| Panel | Fibrous content (%) | Density (kg/m$^3$) | TS (%) | IB (N/mm$^2$) | MOE (kN/mm$^2$) | MOR (N/mm$^2$) |
|---|---|---|---|---|---|---|
| Type 1 fibrous material | 10 | 1628 | 0.6 | 1.0 | 5.8 | 8.8 |
| | 20 | 1554 | 0.6 | 0.9 | 5.3 | 9.3 |
| | 30 | 1518 | 0.7 | 0.7 | 4.7 | 9.8 |
| Type 3 fibrous material | 10 | 1728 | 0.5 | 0.9 | 6.0 | 8.3 |
| | 20 | 1754 | 0.6 | 0.8 | 5.8 | 9.5 |
| | 30 | 1618 | 0.6 | 0.5 | 5.2 | 8.2 |
| Type 4 fibrous material | 10 | 1618 | 0.9 | 1.2 | 5.8 | 12.3 |
| | 20 | 1454 | 0.9 | 0.9 | 5.1 | 10.5 |
| | 30 | 1318 | 1.2 | 0.6 | 4.9 | 10.2 |
| BSEN 634 | | >1000 | 1.5 | 0.5 | 4-4.5 | 9 |

*TS=thickness swelling; IB=internal bond; MOE=modulus of elasticity; MOR=modulus of rupture For cement bonded fibre board, the type 6 material can be used directly, thereby reducing the energy consumption for drying the type 6 material.

Surprisingly, the present inventors found that waste fibre derived from domestic waste had a better compatibility with cement than virgin wood fibre. The virgin wood fibre tested was from Sitka Spruce.

It is well known that wood is composed of cellulose, hemicelluloses, lignin and extractives. Hemicelluloses are complex polysaccharides which have a fairly low molecular weight with a degree of polymerization of 100 to 250. They are branched, amorphous polymers which are soluble in water and alkali. The extractives are also complex mixtures of compounds which vary considerably in their solubility characteristics. The soluble constituents have been commonly quoted as being mainly responsible for the retardation of cement in contact with wood. During the autoclave process, the inventors believe that some of the soluble constituents (if not all) are removed from the waste material, giving a better compatibility of the resultant waste fibre with cement than virgin wood fibre.

In addition to making medium density fibre boards, particle fibre boards and cement bonded fibre boards, the fibre boards made from the waste fibrous materials can also be used to make softboards and plastic fibre boards (examples follow). The softboards can be used as insulation and packaging board products. It is also possible to make gypsum fibre boards, using a process similar to that used for cement bonded fibre boards. The fibre boards produced generally have a light grey to dark grey/black appearance unless they undergo a subsequent surface treatment.

When making products from fibrous waste material, in accordance with the present invention, phase change materials may be added. An example of a phase change material is Micronal® PCM which is available from BASF AG. Micronal® PCM is a plurality of microscopically small polymer spheres containing a wax storage medium in their cores which, incorporated in plasters or gypsum wallboards, for example, melt and solidify and regulate environmental temperatures offering energy savings for cooling and a great comfort in summer.

In the process of the present invention, it is envisaged that virgin raw material could be used in addition to the use of fibrous waste material.

The products prepared by the process of the present invention may be loading bearing (for structural applications) or non-load bearing (for non-structural applications).

D. Manufacture of Softboard Products (Eg. Insulation and Packaging Boards)

Insulation and packaging boards can be produced using the process of the present invention utilising the waste fibrous materials. The properties of the final products can be tailored through different processing parameters.

The type 1 and 3 materials were considered to have properties suitable for use in the manufacture of insulation and packaging boards.

The boards were manufactured from these fibrous materials using the following process steps, after the fibrous material had been deodorised using 10% lime solution. The inventors have found these process steps to be generally applicable to the formation of softboard products using the waste fibrous material obtained from an autoclave process.

a) Refining

This step separates out the fibrous material, depending on the type of material being processed. In this experiment, this step was carried out a pressure of 7 to 8.5 bar for 3 to 5 minutes.

b) Drying

This is performed using a blow-line process which is connected to a continuous, long flash drier.

c) Mixing with a Binding Material

The fibrous materials are blended with resin and other additives. The amount and type of resin added is determined by the solubility parameters of the starting material in order to achieve the desired end product.

The resin must be mixed completely and homogeneously with wax within a short time prior to spreading it onto the fibrous materials. The dosed resin is distributed by means of centrifugal jets to the fibrous materials which are kept in a tumbling movement. The parameters of the process in this experiment were as follows:

Resin: phenolic, bioresin or MDI depending on the uses
Content: 2-10% by mass oven-dry fibrous material.
Additives: Paraffin wax (emulsified) (optional)

d) Puffing

This step may comprise the use of air to separate out the fibrous material.

e) Forming

An air separation system releases the dried fibres into a forming bin and mattresses are formed by the addition of a known mass of fibres into a continuous press steel belt/forming box.

f) Cold Pre-Pressing

This is designed to reduce the thickness of the mat, to increase the contact of fibrous materials and to build an initial strength of the mat to facilitate further processing (eg. conveying and hot pressing). The thickness of the mat is about a quarter to a third that of the original thickness of the mat. Other parameters of the process used in this experiment were:

Temperature: room temperature
Pressure: 13-18 bar
Time: 10-30 sec.
Spring back: 12-25%.

g) Hot Pressing

Temperature: 165-175° C.
Pressure: depending on type of product (density requirements)
The press/heating factor was about 15 sec/mm.

h) Finishing

Finishing includes cutting, thickness monitoring, weighing.

i) Optional Post Treatment

Heat treatment and humidification can be used to improve the quality of the products.

The properties required for the softboards are as follows:
Thickness swelling: 6-10% for 2 hours liquid water immersion
Bending Strength: 0.8-1.3 N/mm$^2$ E. Manufacture of Fiber (Wood) Plastic Composite Products Waste plastic and/or fibrous materials, both derived from autoclave processes, can be used as materials for wood/fibre plastic composites. These composites may comprise 30 to 70% polymeric materials. A generally applicable process, found by the present inventors, is as follows.

Processing: The fibrous materials are refined into fibrous flour or short fibres of consistent size. The fibrous materials are dried to a moisture content in the range of from 2 to 3% by mass. The raw materials are mixed either in batches or by a continuous process, including additives such as lubricants, fire retardants, coupling agents and pigments. The resulting mixture is die injection moulded or compression moulded. The composites can be profile extruded (eg to form solid sections or hollow profiles). The processing temperature is around 150° C. The fibrous waste material is deodorised by being substantially enveloped in the polymeric material.

Performance: Plastic composites have a density ranging from 900 to 1100 kg/m$^3$, a modulus of elasticity MOR ranging from 1000 to 7000 N/mm$^2$ and a modulus of rupture MOR ranging from 10 to 60 N/mm$^2$ at 20° C./65% relative humidity.

The invention claimed is:

1. A process for making composite products from waste material comprising
    obtaining fibrous material produced by the thermal treatment of waste materials with pressurised steam;
    separating out the fibrous material;
    deodorising the fibrous material;
    mixing the fibrous material with a binding material;
    forming the resulting mixture into a shape; and
    curing the shaped mixture.

2. A process as claimed in claim 1, wherein the separating out step is carried out using a raking and shearing process.

3. A process as claimed in claim 1, wherein the separating out step is carried out by puffing and/or refining.

4. A process as claimed in claim 1, wherein the separating out step is carried out by mixing the fibrous material with a powdered material.

5. A process as claimed in claim 4, wherein the powdered material is cement.

6. A process as claimed in claim 1, wherein the deodorising step is carried out by adjusting the moisture and/or temperature of the inner layer of the fibrous material with respect to the outer layer of the fibrous material.

7. A process as claimed in claim 1, wherein the deodorising step is carried out by treating the fibrous material with a lime solution.

8. A process as claimed in claim 1, wherein the deodorising step is carried out by adding calcium carbonate to the fibrous material.

9. A process as claimed in claim 1, wherein the deodorising step is carried out by adding cement to the fibrous material in an aqueous environment.

10. A process as claimed in claim 1, wherein the fibrous material has a moisture content in the range of from 4 to 10% by mass.

11. A process as claimed in claim 1, wherein the fibrous material has a cold water soluble content in the range of from 10 to 20% by mass.

12. A process as claimed in claim 1, wherein the fibrous material has a hot water soluble content in the range of from 9 to 17% by mass.

13. A process as claimed in claim 1, wherein the fibrous material has an alkali soluble content in the range of from 12 to 25% by mass.

14. A process as claimed in claim 1, wherein the fibrous material comprises fibres being less than 10 mm in length.

15. A process as claimed in claim 1, wherein the fibrous material comprises fibres having a mean length of less than 5 mm.

16. A process as claimed in claim 1, wherein the binding material is selected from the group consisting of adhesive, cement and polymeric material.

17. A process as claimed in claim 1, wherein the fibrous material is dried to a moisture content of less than 8% by mass prior to its mixing with the binding material.

18. A process as claimed in claim 1, wherein the forming step comprises pressing and/or extruding the mixture.

19. A process as claimed in claim 18, wherein the pressing step is carried out at an elevated temperature.

20. A process as claimed in claim 1, further comprising a final drying step.

21. A composite product prepared by the process of claim 1 being provided with one or more surface treatments selected from the group consisting of veneering, painting and polishing.

22. A process as claimed in claim 1, wherein the fibrous material has a hot water soluble content in the range of from 10 to 16% by mass.

23. A process as claimed in claim 1, wherein the fibrous material has an alkali soluble content in the range of from 14 to 24% by mass.

24. A process as claimed in claim 1, wherein the fibrous material is dried to a moisture content in the range of from 4 to 8% by mass prior to its mixing with the binding material.

25. A process as claimed in claim 1, wherein the fibrous material is dried to a moisture content of about 6% by mass prior to its mixing with the binding material.

26. A process for making composite products from waste material comprising:
   obtaining fibrous material produced by the thermal treatment of waste materials with pressurised steam;
   separating out the fibrous material by mixing the fibrous material with a powdered material comprising cement;
   deodorising the fibrous material;
   mixing the fibrous material with a binding material;
   forming the resulting mixture into a shape; and
   curing the shaped mixture.

27. A process for making composite products from waste material comprising:
   obtaining fibrous material produced by the thermal treatment of waste materials with pressurised steam;
   separating out the fibrous material;
   deodorising the fibrous material by: treating the fibrous material with a lime solution;
   adding calcium carbonate to the fibrous material; adding cement to the fibrous material in an aqueous environment; or combinations thereof;
   mixing the fibrous material with a binding material;
   forming the resulting mixture into a shape; and
   curing the shaped mixture.

28. The method of claim 1 wherein at least one of the separating out of the fibrous material and the deodorizing of the fibrous material is performed before the mixing of the fibrous material with a binding material.

29. The method of claim 1 wherein at least one of the separating out of the fibrous material and the deodorizing of the fibrous material is performed after the mixing of the fibrous material with a binding material.

30. The method of claim 1 wherein at least one of the separating out of the fibrous material and the deodorizing of the fibrous material is performed during the mixing of the fibrous material with a binding material.

* * * * *